US011506609B2

(12) United States Patent
Stepien et al.

(10) Patent No.: US 11,506,609 B2
(45) Date of Patent: Nov. 22, 2022

(54) METHOD OF DETECTING AND DIAGNOSING THE PROGRESSION OF DIABETES

(71) Applicants: UNIWERSYTET JAGIELLONSKI, Cracow (PL); INSTYTUT FIZYKI JADROWEJ IM. HENRYKA NIEWODNICZANSKIEGO PAN, Cracow (PL)

(72) Inventors: Ewa Lucja Stepien, Giebultow (PL); Agnieszka Kaminska, Cracow (PL); Maciej Roman, Cracow (PL); Czeslawa Paluszkiewicz, Cracow (PL)

(73) Assignees: UNIWERSYTET JAGIELLONSKI, Cracow (PL); INSTYTUT FIZYKI JADROWEJ IM. HENRYKA NIEWODNICZANSKIEGO PAN, Cracow (PL)

( * ) Notice: Subject to any disclaimer, the term of this patent is extended or adjusted under 35 U.S.C. 154(b) by 128 days.

(21) Appl. No.: 16/767,208

(22) PCT Filed: Nov. 29, 2018

(86) PCT No.: PCT/PL2018/050059
§ 371 (c)(1),
(2) Date: May 27, 2020

(87) PCT Pub. No.: WO2019/108076
PCT Pub. Date: Jun. 6, 2019

(65) Prior Publication Data
US 2021/0010939 A1    Jan. 14, 2021

(30) Foreign Application Priority Data

Nov. 29, 2017  (PL) .......................................... 423634

(51) Int. Cl.
*G01N 21/65*    (2006.01)
*G01N 1/40*     (2006.01)
*G01N 33/493*   (2006.01)

(52) U.S. Cl.
CPC .......... *G01N 21/65* (2013.01); *G01N 1/4005* (2013.01); *G01N 1/4077* (2013.01);
(Continued)

(58) Field of Classification Search
CPC ............................. G01N 21/65; G01N 1/4005
See application file for complete search history.

(56) References Cited

PUBLICATIONS

Ying Wang, "Microvesicles and diabetic complications—novel mediators, potential biomarkers and therapeutic targets", 2014 (Year: 2014).*

(Continued)

*Primary Examiner* — Maurice C Smith
(74) *Attorney, Agent, or Firm* — Arrigo, Lee, Guttman & Mouta-Bellum LLP (57) ABSTRACT

The subject of the invention is the method of detecting and diagnosing the progression of diabetes using Raman spectroscopy which involves the examination of the changes in the composition of urinary extracellular vesicles which confirm the existence of the condition and its progression. The invention can be applied in clinical practice, in particular in the early clinical diagnostics of diabetes and in the monitoring of its progression, in particular diabetic nephropathy and advanced renal impairment caused by diabetes.

12 Claims, 2 Drawing Sheets

(52) U.S. Cl.
CPC ... *G01N 33/493* (2013.01); *G01N 2001/4016* (2013.01); *G01N 2201/06113* (2013.01); *G01N 2800/042* (2013.01); *G01N 2800/56* (2013.01)

(56) References Cited

PUBLICATIONS

Charlotte Lawson "Microvesicles and exosomes: new players in metabolic and cardiovascular disease", 2016, Society for Endocrinology (Year: 2016).*

Pardo, F. et al., "Extracellular vesicles in obesity and diabetes mellitus", Molecular Aspects of Medicine 60 (2018) 81-91, Epub Nov. 26, 2017.

Tatischeff, I. et al., "Fast characterisation of cell-derived extracellular vesicles by nanoparticles tracking analysis, cryo-electron microscopy, and Raman tweezers microspectroscopy", Journal of Extracellular Vesicles 2012, 1:19179.

Krafft, CH. et al., "A specific spectral signature of serum and plasma-derived extracellular vesicles for cancer screening", Nanomedicine: Nanotechnology, Biology, and Medicine 13(3) (2017) 835-841, Epub Dec. 10, 2016.

Gualerzi, A. et al., "Raman spectroscopy uncovers biochemical tissue-related features of extracellular vesicles from mesenchymal stromal cells", Scientific Reports 7, Article No. 9820, Aug. 29, 2017.

Musante, L. et al., "Residual urinary extracellular vesicles in ultracentrifugation supernatants after hydrostatic filtration dialysis enrichment" Journal of Extracellular Vesicles, 2016, vol. 6, No. 1, 1267896.

Search Report, PCT/PL2018/050059, dated Mar. 28, 2019.

Written Opinion, PCT/PL2018/050059, dated Mar. 27, 2019.

* cited by examiner

METHOD OF DETECTING AND DIAGNOSING THE PROGRESSION OF DIABETES

The subject of the invention is a spectroscopic method of detecting diabetes and diagnosing its complications on the basis of the changes detected in the composition of urinary extracellular vesicles (UEVs). The invention will be applied in clinical practice, in particular in the early diagnostics of diabetes.

Because of a significant increase in its incidence in 1980-2014, which grew from 108 million to 422 million across the world, diabetes makes one of the most serious threats to human health [1]. In 2011, diabetes was recognized as a global epidemic by the United Nations. Diabetes is one of the so called lifestyle diseases, i.e. common conditions that spread globally because of socio-economic development. According to the WHO report, it is estimated that the number of patients with diabetes (morbidity) has doubled in the recent 30 years, going up from 4.7% in 1980 to 8.5% in 2014, which means that there are 64 million people with diabetes in the European Region of WHO. Each year, about 5% of deaths are caused by a high blood sugar level, which means that 3.7 million people globally die because of diabetes and its complications [1]. Hence, it is essential to be able to detect diabetes in potential patients and then diagnose its complications and progression. This is why diagnostic techniques that enable the diagnosis of the disease (diabetes) and its monitoring are being developed across the world.

Diabetic nephropathy is a chronic kidney disease that develops in patients with diabetes, primarily because of frequent and long-term periods of hyperglycaemia. For patients with diabetes, it is important to regularly monitor kidney function and, if the first (early) symptoms of diabetes arise, implement treatment in order to stop the disease progression. The onset of diabetic nephropathy is asymptomatic and the glomerular filtration rate is close to normal in the early stage of the disease.

In many cases, diabetic nephropathy leads to end-stage kidney failure, i.e. dialysis. In Poland, there are over 3.5 thousand diabetic patients undergoing long-term dialysis therapy because of kidney failure. The stages of diabetic nephropathy are differentiated on the basis of the deteriorating glomerular filtration rate: GFR goes down from the level of 90 to 60 mL/min/1.73 m$^2$ in the patients in the 2$^{nd}$ stage of the disease to below 15 mL/min/1.73 m$^2$ in the patients with end-stage kidney failure [1]. So far, the most important screening test for the patients who were not diagnosed with evident proteinuria on the basis of urine tests has been the level of albumin/creatinine in the early morning (or random) urine sample. Increased urinary excretion of albumin (albumin/creatinine>30 mg/g) must be confirmed—2 positive results are needed for the diagnosis. It is recommended that the first screening test for albuminuria be performed 5 years after they were diagnosed with the disease in the case of patients with type 1 diabetes, or at the moment of the diagnosis in the case of patients with type 2 diabetes. According to WHO (2016), it is estimated that about 25% of the new cases of diabetes are not diagnosed, which leads to the underestimation of the number of patients. In Poland, it is estimated that about 30% of patients do not know that they have diabetes. The risk of diabetic nephropathy and cardio-vascular complications may range from two- to five-fold, depending on the patient's gender and age.

Another important social aspect is the quality of life of diabetic patients. The longer people live with undiagnosed diabetes, the worse is the starting point for treatment and the patient's condition at the onset of the therapy. According to the WHO diabetes report, screening tests for the early detection of diabetic complications should be included in all guidelines on the diagnosing and treatment of diabetes.

Raman spectroscopy has been extensively applied in biological tests, primarily in the examination of the structure of nucleic acids—DNA and RNA, protein complexes with nucleic acids (ribonucleoproteins) [1], lipids and carotenoids [2, 3] and other chemical compounds (metabolites) [1]. In laboratory medicine, Raman spectroscopy is increasingly applied, primarily to monitor the drug level and identify pathogens [1], but more and more often it is used to diagnose tumours, including pharyngeal tumours [6], breast cancer [1, 2], stomach cancer [3], skin cancer [4], osteoporosis [5], diabetes [6, 7], atherosclerosis [5, 8] and to diagnose kidney function [9, 10]. Raman spectroscopy is also used in forensic tests to identify blood traces and other biological traces [1, 2, 3]. A new and unique application of Raman spectroscopy includes the analysis of molecular signatures of extracellular vesicles, which was performed on the samples of tumour cell line cultures and the samples of the patients' serum [1].

Microvesicles or extracellular vesicles (EVs) are tiny, spherical, membranous structures of the diameter of 20-1000 nm which are released to the intercellular space [1]. This term refers both to the microvesicles that multiply directly from the cellular membrane during the cell's life cycle—ectosomes or during the cell's programmed death—apoptic blebs and the intercellular vesicles—exosomes released from multivesicular bodies [1]. Regardless of their different characteristics in terms of size (exosomes: 30-100 nm, ectosomes: 100-1000 nm, apoptic blebs: 500-1000 nm), microvesicles share a number of common features, such as a two-layer lipid membrane with lipids and nucleic acids inside these structures [1, 2]. The cargo transported by microvesicles, which reflects the status of the excreting cell, is delivered to the target cell and takes an active part in intracellular signalling [3]. Extracellular vesicles may be obtained from all body fluids (e.g. blood, urine, saliva or cerebrospinal fluid) and their analysis may replace the invasive and expensive technique of traditional biopsy in the future. The diagnostics of genitourinary diseases may also be performed on the basis of the analysis of the material coming from urinary extracellular vesicles—UEVs [3, 4, 5].

A review provided by Lawson (2016) presents the application of various populations of EVs as biomarkers of cardiovascular and metabolic diseases without indicating any specific methods for the isolation of EVs from clinical samples or defining Raman spectroscopy as a research technique [3]. Another review proposes that EVs serve as diagnostic markers for obesity or diabetes with the indication that urinary extracellular vesicles are the carriers of microRNA related to the disease [3].

In the scientific publication by Krafft (2016), extracellular vesicles were applied as diagnostic biomarkers in order to differentiate tumour patients. Raman spectroscopy was used to carry out a comparative analysis of extracellular vesicles collected from patients with tumours and from healthy individuals. To this end, two different fractions of EVs enriched with exosomes and ectosomes were isolated from blood serum and plasma using differential centrifugation. The change of the profile reflecting the protein structure (alpha-helix-rich, beta-sheet-rich) was used to detect prostate cancer.

The scientific publication of Brindh (2017) describes the application of Raman spectroscopy (for high wave numbers, HWVN) to characterise urine samples of healthy individuals, pre-cancer patients and cancer patients. It was observed that flavoproteins, metabolites, tryptophan and phenylalanine in urine are related to the differences in Raman spectra between the healthy group and the cancer group. It should be noted that the analysis was performed for the spectra with high wave numbers (2600-3500 cm−1).

Saatkamp's publication (2016) [16] provides information on the application of Raman spectroscopy to assess the concentration of urea and creatinine in urine, which may further be used to diagnose nephropathy.

In her publication, Kamińska (2016) [28] presented studies indicating the relationship between the density of EVs, their size distribution and the progression of early kidney failure in patients with type 2 diabetes. The study involved patients with controlled and uncontrolled diabetes (additionally, with kidney failure and without kidney failure). The diameter and number of EVs was evaluated using the Tunable Resistive Pulse Sensing technique. The density of EVs was evaluated using a transmission electron microscope. It was demonstrated that urine is rich in EVs. Moreover, EVs were used to differentiate patients with controlled and uncontrolled diabetes, but the differentiation was based on the number and size distribution of EVs, which made it also possible to reflect the deterioration of kidney function suggesting that EVs may be applied as biomarkers of kidney failure.

Considering the above described state of the art, there is still demand for methods that would enable early, non-invasive and low-cost diagnosis of diabetes and its monitoring. The early diagnosis of diabetic nephropathy and the extent of its progression is especially important.

Unexpectedly, such a method was obtained in this invention.

The subject of the invention is a method of detecting diabetes and diagnosing its complications wherein a change in the structure of extracellular vesicles is examined in a tissue or liquid sample collected from the patient, which confirms the presence of diabetes and its progression.

In an advantageous embodiment, the composition of urinary extracellular vesicles is examined (UEV).

In an advantageous embodiment, the method in the invention involves the following stages:
a) Extracellular vesicles are isolated from the urine sample,
b) Raman spectra are registered and the distribution of the intensity of characteristic bands is analysed,
c) If it is confirmed that the RI value for the Raman band intensity is lower than the RI value for the Raman band obtained in an identical way for the sample collected from a healthy individual, the patient is diagnosed with diabetes.

In an advantageous embodiment, in stage a), the urine sample is centrifuged at 2000×g for about 30 minutes.

In an advantageous embodiment, in stage a), the urine sample is concentrated using a large-pore dialysis membrane permeable for molecules with the average molecular weight below 1000 kDa (MWCO), which is followed by washing.

In an advantageous embodiment, the washing solution contains colloidal silver (0.1 mg of silver chloride and 4.5 mg of sodium dichloroisocyanurate per litre of the urine sample) is applied.

In an advantageous embodiment, the characteristic bands in the Raman spectrum are located within the following ranges: from 980 cm$^{-1}$ to 1020 cm$^{-1}$, from 1110 cm$^{-1}$ to 1140 cm$^{-1}$, from 1420 to 1470 cm$^{-1}$ and from 1565 cm$^{-1}$ to 1710 cm$^{-1}$, In an advantageous embodiment, in stage c), in order to determine the change in the intensity of the Raman band, the value of RI is calculated according to the following formula:

$$RI = \frac{I_{AmidI}}{I_{Phenylalanin}} \times a + \frac{I_{Lipids}}{I_{Phenylalanin}}.$$

In an advantageous embodiment, in stage c), it is accepted that the values of RI for the group of healthy individuals are above 1000, from 1144 to 1164.

In an advantageous embodiment, in stage c), it is accepted that the values of RI for the group of patients are below 600.

In an advantageous embodiment, in stage c), it is accepted that the values of RI for the group of patients with controlled diabetes are from 550 to 600.

In an advantageous embodiment, in stage c), it is accepted that the values of RI for the group of patients with uncontrolled diabetes are from 390 to 410.

In an advantageous embodiment, in stage c), it is accepted that the values of RI for the group of patients with diabetic nephropathy are below 600.

In an advantageous embodiment, in stage c), it is accepted that the values of RI for the group of patients with advanced diabetic nephropathy with the glomerular filtration rate below 46 mL/min/1.73 m$^2$ are below 300.

Unexpectedly, over the course of work that led to the development of this invention, it was determined that the change in the band intensity of the Raman spectrum, which is a consequence of the differences in the molecular composition of UEVs, as compared with UEVs of healthy individuals confirms the presence of the disease and makes it possible to differentiate between controlled and uncontrolled diabetes and diagnose its progression, in particular identify diabetic nephropathy and advanced kidney failure caused by diabetes.

The method of this invention makes it possible to differentiate between diabetic patients and the control group as well as between patients with controlled and uncontrolled diabetes by means of the analysis of urinary extracellular vesicles (UEVs) using Raman spectroscopy.

EXAMPLE 1

Diagnosing the Presence of Diabetes, Controlled Diabetes and Uncontrolled Diabetes The Description of the Group Under Examination The group under examination were patients with type 2 diabetes (n=45). The patients were divided into 2 groups according to the diabetes control level based on the level of glycated haemoglobin (HbA1C) following the 2016 guidelines of the Polish Diabetes Association: the group with controlled diabetes (CD) (n=19) and the group with uncontrolled diabetes (UD) (n=26) where HbA1C>7%. The group of patients was compared with the control group (n=6). Table 1 shows the characteristics of the group under examination.

Additionally, the patients' history was collected, which included demographic data, arterial blood pressure, BMI, dietary habits and addictions (smoking and alcohol consumption) as well as the anti-diabetic treatment and drug therapy (potassium-sparing diuretics, loop diuretics, thiazide and thiazide-like diuretics, beta-blockers, ACEI, Ca antagonists, Na/K ATPase inhibitors, vasodilating diuretics, clopidogrel, acetosalicylic acid and statins), information on the surgeries and surgical procedures undergone by patients, including coronary artery bypass grafts (CABG) and percutaneous coronary interventions (PCI), as well as comorbidities and cancer. The patients diagnosed with the following conditions during the examination or history collection were excluded from the study:
- diagnosis or suspicion of a recent bacterial or viral infection,
- cancer,
- a cardio-vascular incident or surgery within 6 months prior to the history collection,
- signs of liver impairment,
- steroid and non-steroid anti-inflammatory therapy,
- surgical treatment of obesity,
- hormonal replacement therapy in the case of women,
- autoimmune diseases (i.e. chronic arthritis, antiphospholipid syndrome).

The Condensation and Isolation of Urinary Extracellular Vesicles from Urine Samples Samples of morning urine of about 250 ml were collected from the patients and the healthy volunteers. Initially, the urine was centrifuged at 2000×g for about 30 minutes in order to remove epithelial cells, bacteria and urinary deposits. Then, the urine was concentrated using hydrostatic filtration/dialysis (HDF), a method in which urine is filtrated using a dialysis membrane with large-diameter pores permeable to molecules whose molecular weight is below 1000 kDa (MWCO). After volume reduction, the sample was washed using deionised water and, again, reduced to the volume of a few millilitres. In another variant, it is possible to use colloidal silver containing silver chloride and sodium dichloroisocyanurate in the amounts of, respectively, 0.1 mg and 4.5 mg per every litre of the urine sample, in order to chemically inactivate the remaining bacteria.

The Evaluation of the Presence of UEVs Using the Transmission Electron Microscope (TEM)

Figure 1:
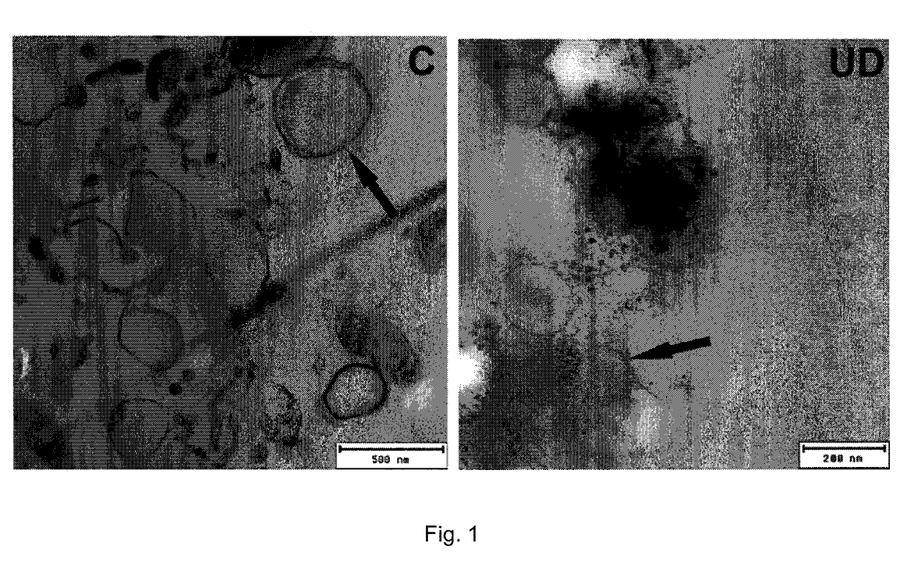
FIG. 1 shows the microphotograph of urinary extracellular vesicles (UEVs) obtained by means of centrifugation from a healthy individual (C) and a person with uncontrolled type 2 diabetes (UD)

The deposit samples were centrifuged in Eppendorf tubes and stabilised in 2.5% glutaraldehyde (cat. no. G5882, Sigma-Aldrich, St. Louis, USA) in 0.1 M of cacodylic buffer (cat. no. C4945, Aldrich, St. Louis, USA) for 2 hours in room temperature, and then in 1% solution of osmium tetrachloride ($OsO_4$) for 1 hour. The samples were dehydrated in ethanol and embedded in PolyBed 812 in 68° C. Snippets for analysis were placed on a mesh (300 mesh grids). Next, the snippets were contrasted using uranyl acetate and lead citrate. The JEOL JEM 2100HT electronic microscope (JEOL Ltd., Tokio, Japonia) with accelerating voltage of 80 kV was used for observation. This stage is presented in FIG. 1.

Raman Spectroscopy and the Analysis of Characteristic Bands

Figure 2:
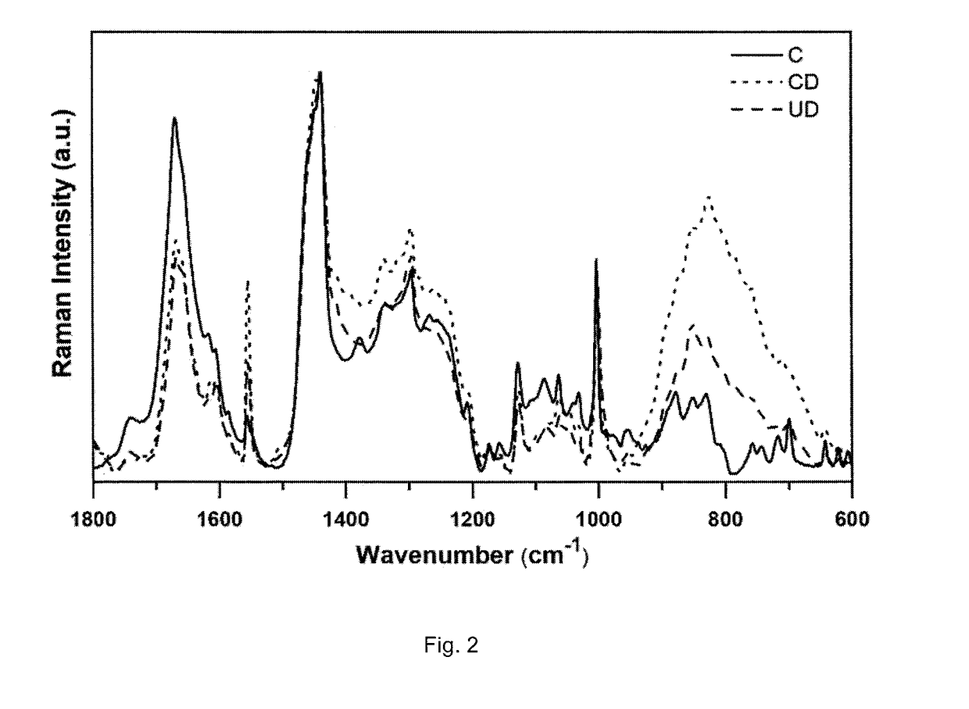
FIG. 2 shows the Raman spectra of the pooled samples obtained from patients with controlled type 2 diabetes (CD), patients with uncontrolled diabetes (UD) and 2 samples from the healthy control group (C)
Figure 3:
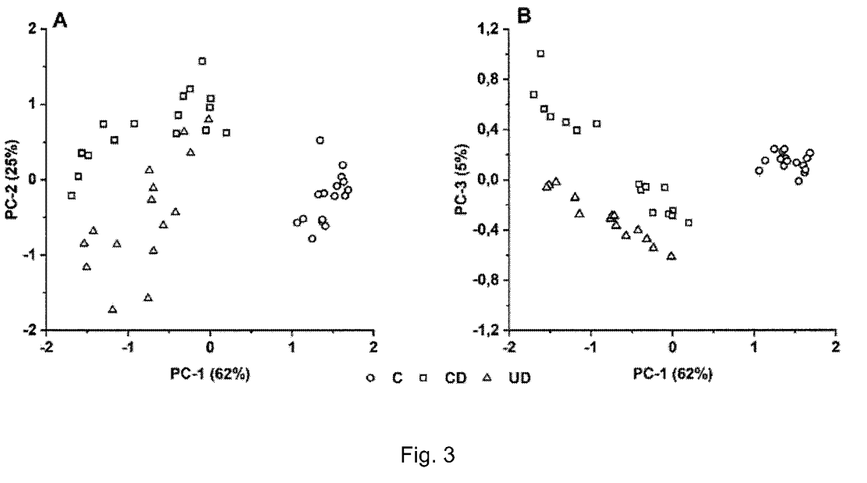
FIG. 3 shows the principle component analysis (PCA) of the Raman spectra obtained from patients with CD (■), UD (▲) and from the control group C (•)—the graphs are in non-nominal units and present the share of the component, a variable in this case (band intensity [a.u.]), in the model of a covariance matrix.

Raman spectra were registered using the Renishaw InVia Raman spectrometer equipped with an optical confocal microscope with the Leica N PLAN EPI dry lens (100×, NA 0.85). The laser emitting the light of the wavelength of 532 nm was cooled using air; the laser power in the sample position was about 15 mW. The CCD detector was cooled thermoelectrically to the temperature of $-70°$ C. A drop of the UEV suspension was placed on the $CaF_2$ window and left there until the water evaporated. Each dried sample was measured in at least 15 randomly selected places. Eventually, 100 scans with the exposure time of 20 s and the resolution of about 1.5 cm-1 were collected from each place. The spectrometer was calibrated on the basis of the location of the Raman band of the silicon plate inside the device. A principle component analysis (PCA) was carried out using the Unscrambler X 10.3 software (CAMO AS, Norway). Prior to PCA, Raman spectra were adjusted by cutting off the baseline, and, subsequently, they were smoothed and normalised. The registered Raman spectra were presented in FIG. 2. Table 2 shows the intensity of the characteristic bands that are important for the differentiation of individual sample groups, which was concluded on the basis of PCA. FIG. 3 shows the principle component analysis of the Raman spectra registered for the samples obtained from the patients. It clearly shows that individual points gather in clusters that include the individual groups under examination.

TABLE 1

The characteristics of the groups under examination as regards biochemical and epidemiological parameters

| Parameter | Control (C) n = 6 | Controlled diabetes (CD) n = 19 | Uncontrolled diabetes (UD) n = 26 | p-value |
|---|---|---|---|---|
| Gender (M/F) | 6 | 13/6 | 18/8 | — |
| Age [years] | 51 (7) | 62 (16) | 61 (13) | 0.099 |
| HbA1C [%] | — | 44 (42-48) | 68 (62-73) | <0.0001 |
| Glucose in serum (mmol/L) | 5 (5-6) | 7 (6-8) | 9 (7-11) | <0.0001 |
| Albumin in urine [mg/L] | 6 (4-13) | 6 (1-10) | 30 (12-244) | 0.0002 |
| Creatinine in urine [mM] | 12 (9-16) | 5 (4-10) | 6 (5-9) | 0.008 |
| Creatinine in serum [µM] | 69 (60-85) | 73 (62-87) | 77 (61-104) | 0.546 |
| GFR [mL/min/1.73 m$^2$] | 84 (76-100) | 89 (68-103) | 86 (64-100) | 0.921 |

TABLE 2

A list of characteristic bands for which statistically significant differences were observed in Raman spectra

| Band position | Average band intensity [a.u.]# | | | P |
|---|---|---|---|---|
| | C | CD | UD | |
| 1565-1710 cm$^{-1}$ Amid I | 0.303 (0.016) | 0.223 (0.055)* | 0.247 (0.024)* | 4.38E−7 |

TABLE 2-continued

A list of characteristic bands for which statistically significant differences were observed in Raman spectra

| | Average band intensity [a.u.][#] | | | |
|---|---|---|---|---|
| Band position | C | CD | UD | P |
| 1420-1470 cm$^{-1}$ Lipids | 0.115 (0.006) | 0.111 (0.007) | 0.138 (0.019)* | 3.82E−5 |
| 1110-1140 cm$^{-1}$ Proteins | 0.014 (0.001) | 0.015 (0.003) | 0.017 (0.003)* | 0.024 |
| 980-1020 cm$^{-1}$ Phenylalanine | 0.023 (0.005) | 0.034 (0.006)* | 0.053 (0.007)* | 2.97E−9 |

[#]Average values of the band intensity have been normalised and are expressed in arbitrary units [a.u.]
*intensity values that differ from control values in a statistically significant way for the level of significance α = 0.05; the groups were compared between each other using the non-parametric Kruskal-Wallis test; additionally, the U Mann-Whitney test was applied for both groups.

The Determination of RI—Ratio Intensity—which Differentiates the Group of Patients with Controlled Diabetes (CD) and Uncontrolled Diabetes (UD) from the Control Group (C)

To determine the value of RI, which differentiates the CD and UD group from the control group C in an arbitrary way, the following formula was used:

$$RI = \frac{I_{AmidI}}{I_{Phenylalanine}} \times a + \frac{I_{Lipids}}{I_{Phenylalanine}} \quad (1)$$

where:
$I_{AmidI}$—is the value of the band intensity for Amid I (1565-1710 cm$^{-1}$)
$I_{Phenylalamine}$—is the value of the band intensity for phenylalanine (980-1020 cm$^{-1}$)
$I_{Lipids}$—is the value of the band intensity for lipids (1420-1470 cm$^{-1}$)
a—is the weight factor determined as the quotient of statistical significance (p) for the difference between the intensity of bands $I_{Amid\ I}$ and $I_{Lipids}$ between the group of patients and the group of healthy individuals; in this case a=87.2

$$a = \frac{p_{Lipids}}{p_{AmidI}}$$

$$a = 87.2$$

The probability value (p) was calculated in the OriginPro 2017 programme (according to the algorithm for the Kruskal-Wallis test).
The Kruskal-Wallis test statistics in the OriginPro 2017 programme is calculated according to the following formula:

$$H = \frac{12}{N(N+1)} \sum_{j=1}^{k} \frac{R_j^2}{n_j} - 3(N+1)$$

H— the Kruskal-Wallis test
N— the total number of observations
k—the number of the groups compared
$n_j$—the number of observations in a given group
$R_j$—the total of ranks in a given group
On the basis of the equation, IR for group C, CD and UD was determined:

$RI_C$=1154±10.5

$RI_{CD}$=575±24.7

$RI_{UD}$=409±9.9

The values were provided with the approximation error experimentally determined.
On the basis of this, the threshold value for diabetes was determined:

RI<600

EXAMPLE 2

Diagnosing the Progression of Diabetes—Identifying the Presence of Diabetic Nephropathy and Determining its Progression An additional analysis of the variability of the urinary extracellular vesicle spectra using Raman spectroscopy was performed for the extended group of patients with type 2 diabetes (n=18) and various degrees of renal impairment in diabetic nephropathy defined according to the value of the glomerular filtration rate (GFR).
Group 5<15 ml/min/1.73 m$^2$ (n=4)
Group 4 15-30 ml/min/1.73 m$^2$ (n=7)
Group 3 31-45 ml/min/1.73 m$^2$ (n=2)
Group 2 46-60 ml/min/1.73 m$^2$ (n=1)
Group 1 61-90 ml/min/1.73 m$^2$ (n=4)
and the control group>90 ml/min/1.73 m$^2$ (n=6)
Clinical and epidemiological data can be found in Table 3.

TABLE 3

The characteristics of the groups of patients under examination as regards selected biochemical and epidemiological parameters.

| Parameter | Control | 5 | 4 | 3 | 2 | 1 | p |
|---|---|---|---|---|---|---|---|
| Gender (F/M) | 1/5 | 2/2 | 2/5 | 2/0 | 0/1 | 2/2 | — |
| Age (years) | 55 (5) | 70 (9) | 67 (11) | 81 (3)† | 56 | 66 (10) | 0.02463 |
| Creatinine in serum (μmol/l) | 94 (80-95) | 431†* (370-606) | 220†* (197-254) | 97 (35-45) | 126 | 76* (56-101) | 0.00324 |
| GFR (ml/min/1.73 m$^2$) | 90 (84-111) | 11†* (7-12) | 23†* (21-26) | 40 (35-45) | 55 | 83* (80-87) | 0.00237 |
| Glucose (mmol/l) | 5.3 (5.1-5.4) | 15.9†* (10.6-19.0) | 7.6† (6.8-9.3) | 5.7 (5.4-6.0) | 6.8 | 8.2† (7.9-11.1) | 0.00758 |
| hsCRP (mg/l) | 0.34 | 3.3† (2.5-7.1) | 6.8† (4.5-10.3) | 2.6 (2.5-2.7) | 0.9 | 18.5†* (14.0-23.0) | 0.09321 |
| LDL CHOL (mmol/l) | 3.2 | 1.9 (1.5-2.7) | 3.4 (2.7-3.7) | 2.6 (2.5-2.7) | 3.4 | 2.3 (0.9-3.0) | 0.10374 |

TABLE 3-continued

The characteristics of the groups of patients under examination as regards selected biochemical and epidemiological parameters.

| Parameter | Control | 5 | 4 | 3 | 2 | 1 | p |
|---|---|---|---|---|---|---|---|
| HDL CHOL (mmol/l) | 1.31 | 0.7 (0.6-0.8) | 0.9 (0.9-1.0) | 1.2 (1.1-1.3) | 1.5 | 1.1 (0.8-2.0) | 0.08204 |
| TG (mmol/l) | 0.7 | 2.3 (1.3-3.5) | 1.4 (1.1-2.8) | 1.6 (1.6-1.7) | 2.5 | 1.1 (0.9-1.9) | 0.38717 |
| CHOL (mmol/l) | 4.8 | 3.7 (3.74.1) | 4.8 (4.3-4.9) | 4.5 (4.3-4.9) | 6.0 | 3.6 (2.9-5.5) | 0.29512 |
| Albumin in urine (mg/l) | 4.4 (3.9-4.4) | 896.9†* | 254†* (39.5-2880) | 8.8 (2.0-15.5) | — | 49.6 (30.4-257) | 0.0665 |

The groups were compared between one another using ANOVA or Kruskal-Wallis tests.
†a statistically significant difference for the group as compared with the control group
*a statistically significant difference for the group as compared with the remaining groups of patients The table above shows that the patients with the highest level of renal impairment (Group 5 and Group 4) were significantly different from the remaining groups of patients with regard to:

blood glucose concentration the concentration of albumin in urine

Next, the Raman spectra were registered (just like before) for the range of 400-1800 cm$^{-1}$, for the urinary extracellular vesicles isolated from the morning urine samples (80-100 mL) collected from the patients, individually for each patient.

Figure 4:
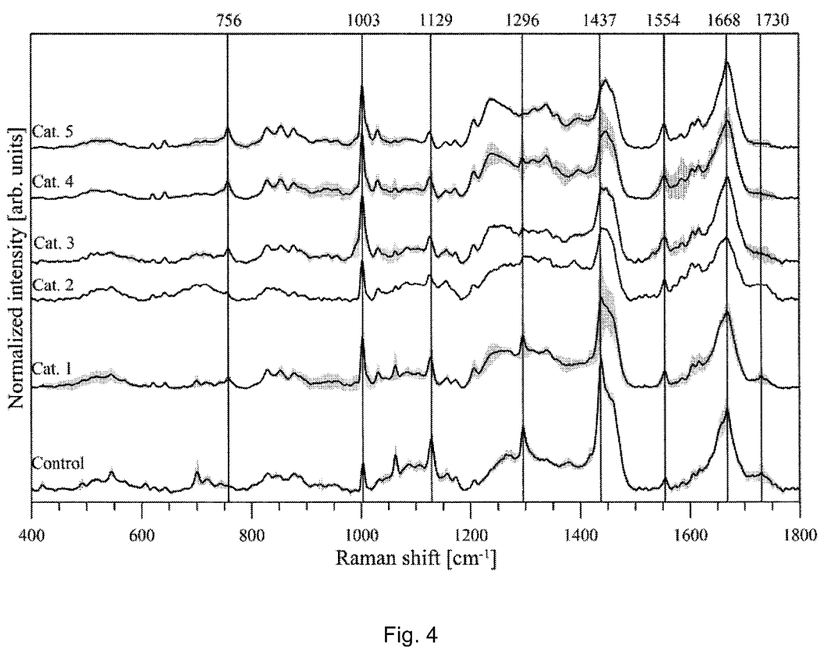
FIG. 4 shows the recording of the averaged spectra for 5 groups of patients classified according to the degree of kidney failure.

Then the spectra were divided into 5 groups according to the criterion of renal impairment (GFR), the spectra were averaged and the average spectra for each group were plotted. The graphs can be found in FIG. 4, which shows the recording of the averaged spectra for 5 groups of patients classified according to the degree of kidney failure: 1) 61-90 ml/min/1.73 m$^2$; 2) 46-60 ml/min/1.73 m$^2$; 3) 31-45 ml/min/1.73 m$^2$; 4) 15-30 ml/min/1.73 m$^2$; 5) <15 ml/min/1.73 m$^2$.

On the basis of the spectra determined, the analysis of the average values of the area under the curve (AUC) was carried out for the selected bands representing metabolites present in urinary extracellular vesicles of the patients with diabetes and various degrees of renal impairment. Additionally, the analysis involved the values of the average intensity of the selected bands.

On the basis of the biochemical parameters determined and the analysis of Raman spectra, the correlation analysis using a parametric test (a Pearson correlation test) for the AUC values in individual ranges and the biochemical marker concentration values was performed. On the basis of the calculations performed, it can be concluded that, for the patients with diabetes, the values for the Raman spectrum band corresponding to nucleic acids (DNA) correlate significantly with:

eGFR (negative correlation), the concentration of creatinine in serum (positive correlation), which corresponds to the level of progression of kidney failure.

Moreover, for the patients with diabetes, the values of the Raman spectrum corresponding to:

lipids (1282-1305 cm$^{-1}$) and proteins and lipids (1403-1502 cm$^{-1}$)

correlate significantly (positive correlation) with the concentration of triglycerides (TG), which corresponds to the level of progression of dyslipidaemia in diabetes.

Determining RI to Assess the Degree of Renal Impairment for Averaged Spectra

The additional analyses carried out for the group of patients with diabetic nephropathy which show the application of the introduced RI value to the assessment of the degree of renal impairment in patients with diabetes.

The following equation was used to determine the value of RI, which differentiates, in an arbitrary way, the CD (controlled diabetes) and UD (uncontrolled diabetes—uncontrolled blood sugar level) groups from the control group C:

$$RI = \frac{I_{AmidI}}{I_{Phenylalanin}} \times a + \frac{I_{Lipids}}{I_{Phenylalanin}} \quad (1)$$

where:

$I_{Amid\ I}$—is the value of the band intensity for Amid I (1565-1710 cm−1)

$I_{Fenyloalanina}$—is the value of the band intensity for phenylalanine (980-1020 cm$^{-1}$)

$I_{Lipidy}$—is the value of the band intensity for lipids (1420-1470 cm$^{-1}$)

a—is the weight factor determined as the quotient of the statistical significance (p) for the difference between the intensity of the bands $I_{AmidI}$ and $I_{Lipids}$ between the groups of patients and the group of healthy individuals; in this case a=87.2

$$a = \frac{p_{Lipids}}{p_{AmidI}}$$

a=87.2

On the basis of the area under the curve (AUC), the parameters determined and the average band intensity (I), RI for individual groups of patients (Table 4) was determined using formula (1)

TABLE 4

| | Control | 5 | 4 | 3 | 2 | 1 |
|---|---|---|---|---|---|---|
| RI calculated for AUC | 1722 | 569 | 568 | 524 | 986 | 733 |
| RI calculated for I average | 331 | 109 | 108 | 100 | 187 | 140 |

On the basis of the RI values calculated, it was established that the threshold value for diabetic nephropathy was RI<600.

The patient with RI<300 is diagnosed with advanced renal impairment with the glomerular filtration rate (GFR) below 46 mL/min/1.73 m$^2$.

1 van der Pol E, Böing A N, Harrison P, Sturk A, Nieuwland R. Classification, functions, and clinical relevance of extracellular vesicles. Pharmacol Rev. 2012; 64(3); 676-705.

2 van der Pol E, Böing A N, Gool E L, Nieuwland R. Recent developments in the nomenclature, presence, isolation, detection and clinical impact of extracellular vesicles. i inni. 1, 2016, J Thromb Haemost. 2016; 14(1); 48-56.

REFERENCE LITERATURE

1. World Health Organization. Global report on diabetes. WHO Library Cataloguing-in-Publication Data, Geneva 2016. ISBN 978 92 4 156525 7.
2. Pilarski Ł, Bogdański P, Pupek-Musialik D. Przewlekta choroba nerek u chorych na cukrzycę typu 2—epidemiologia, patogeneza i konsekwencje kliniczne. Forum Zab. Met. 2011; 3:192-197
3. Thomas G J, Agard D A. Quantitative analysis of nucleic acids, proteins, and viruses by Raman band deconvolution. Biophys J. 1984; 46:763-768.
4. Bonetti A, Bonifacio A, Della Mora A, Livi U, Marchini M, Ortolani F. Carotenoids co-localize with hydroxyapatite, cholesterol, and other lipids in calcified stenotic aortic valves. Ex vivo Raman maps compared to histological patterns. Eur J Histochem. 2015; 59(2):2505.
5. Kochan K, Marzec K M, Chruszcz-Lipska K, Jasztal A, Maslak E, Musiolik H, Chłopicki S, Baranska M. Pathological changes in the biochemical profile of the liver in atherosclerosis and diabetes assessed by Raman spectroscopy. Analyst. 2013; 138(14):3885-90
6. Brindha E, Rajasekaran R, Aruna P, Koteeswaran D, Ganesan S. High wavenumber Raman spectroscopy in the characterization of urinary metabolites of normal subjects, oral premalignant and malignant patients. Spectrochim Acta A Mol Biomol Spectrosc. 2017; 171:52-59.
7. Neugebauer U, Rösch P, Popp J. Raman spectroscopy towards clinical application: drug monitoring and pathogen identification. Int J Antimicrob Agents. 2015; 46 Suppl 1:S35-9
8. Haka A S, Shafer-Peltier K E, Fitzmaurice M, Crowe J, Dasari R R, Feld M S. Diagnosis breast cancer by using Raman Spectroscopy. Adv Drug Deliv Rev. 2015; 89: 121-134.
9. Abramczyk H, Brozek-Pluska B. New look inside human breast ducts with Raman imaging. Raman candidates as diagnostic markers for breast cancer prognosis: Mammaglobin, palmitic acid and sphingomyelin. Anal Chim Acta. 2016; 909:91-100.
10. Yao H, Tao Z, Ai M, et al. Raman spectroscopic analysis of apoptosis of single human gastric cancer cells. Vibrat Spec. 2009; 50: 193-197
11. Zeng H, Lui H, McLean D I. Skin cancer detection using in vivo Raman spectroscopy, SPIE Newsroom. 2011; DOI: 10.1117/2.1201104.003705
12. Lloyd W R, Agarwal S, Nigwekar S U, Esmonde-White K, Loder S, Fagan S, Goverman J, Olsen B R, Jumlongras D, Morris M D, Levi B. Raman spectroscopy for label-free identification of calciphylaxis. J Biomed Opt. 2015; 20(8):80501.
13. Dingari N C, Horowitz G L, Kang J W, Dasari R R, Barman I. Raman spectroscopy provides a powerful diagnostic tool for accurate determination of albumin glycation. PLoS One. 2012; 7(2):e32406.
14. Barman I, Dingari N C, Kang J W, Horowitz G L, Dasari R R, Feld M S. Raman spectroscopy-based sensitive and specific detection of glycated hemoglobin. Anal Chem. 2012; 84(5):2474-82.
15. Alderico R, Sokki S. Raman spectroscopy for diagnosis of atherosclerosis: a rapid analysis using neural networks. Med Eng Phys. 2005; 27: 237-244
16. Hong T D, Phat D, Plaza P, Daudon M, Dao N Q. Identification of urinary calculi by Raman laser fiber optics spectroscopy. Clin Chem. 1992 February; 38(2): 292-8
17. Saatkamp C J, de Almeida M L, Bispo J A, Pinheiro A L, Fernandes A B, Silveira L Jr. Quantifying creatinine and urea in human urine through Raman spectroscopy aiming at diagnosis of kidney disease. J Biomed Opt. 2016 March; 21(3):37001.
18. Muro C K, Lednev I K. Identification of individual red blood cells by Raman microspectroscopy for forensic purposes: in search of a limit of detection. Anal Bioanal Chem. 2017; 409(1):287-293.
19. Sikirzhytskaya A, Sikirzhytski V, Lednev I K. Raman spectroscopic signature of vaginal fluid and its potential application in forensic body fluid identification. Forensic Sci Int. 2012; 216(1-3):44-8.
20. Virkler K, Lednev I K. Raman spectroscopic signature of semen and its potential application to forensic body fluid identification. Forensic Sci Int. 2009; 193(1-3):56-62.
21. Krafft C, Wilhelm K, Eremin A, Nestel S, von Bubnoff N, Schultze-Seemann W, Popp J, Nazarenko I. A specific spectral signature of serum and plasma-derived extracellular vesicles for cancer screening. Nanomedicine. 2017; 13(3): 835-841 doi: 10.1016/j.nano.2016.11.016.
22. Théry C, Ostrowski M i Segura E. Membrane vesicles as conveyors of immune responses. Nat Rev Immunol. 2009; 9:581-93.
23. Colombo M, Raposo G i Théry C. Biogenesis, secretion, and intercellular interactions of exosomes and other extracellular vesicles., Annu Rev Cell Dev Biol; 2014; 30:255-89.
24. van der Pol E, Böing A N, Harrison P, Sturk A, Nieuwland R. Classification, functions, and clinical relevance of extracellular vesicles. Pharmacol Rev. 2012; 64(3); 676-705.
25. van der Pol E, Böing A N, God E L, Nieuwland R. Recent developments in the nomenclature, presence, isolation, detection and clinical impact of extracellular vesicles. i inni. 1, 2016, J Thromb Haemost. 2016; 14(1); 48-56.
26. Lee J-K, Jang J-Y, Jeon Y-K, Kin C-W. Extracellular Vesicles as an Emerging Paradigm of Cell-to-Cell Communication in Stem Cell Biology. Journal of Stem Cell Research & Therapy. 2014; 4:206. doi:10.4172/2157-7633.1000206
27. Koppers-Lalic D, Hackenberg M, de Menezes R, et al. 1 Non-invasive prostate cancer detection by measuring miRNA variants (isomiRs) in urine extracellular vesicles. Oncotarget. 2016; 7(16):22566-78.
28. Delić D Eisele C, Schmid R, Baum P et al. Urinary Exosomal miRNA Signature in Type II Diabetic Nephropathy Patients. 3, 2016, PLoS One. 2016; 11(3): e0150154.
29. Kamińska A, Platt M, Kuśnierz-Cabala B et al. Urinary Extracellular Vesicles: Potential Biomarkers of Renal Function in Diabetic Patients. J Diabet Res. 2016; 5741518, 12 pp, doi.org/10.1155/2016/5741518
30. Lawson Ch, Vincencio J M, Zeellon D M, Davidson S M. Microvesicles and exosomes: new players in metabolic and cardiovascular disease. J Endocrin. 2016; 228, R57-R71
31. Pardo F, Villalobos-Labra R, Sobrevia B et al. Extracellular vesicles in obesity and diabetes mellitus, Mol Asp Med. 2018; 60:81-91.

32 Polskie Towarzystwo Diabetologiczne: Zalecenia kliniczne dotyczące postępowania u chorych na cukrzycę. Diab Klin. 2016; 5 (Supl. A): A1-A76.

The invention claimed is:

1. A method of detecting and diagnosing diabetes comprising the following steps:
   a) Urinary extracellular vesicles (UEV) are isolated from the urine sample,
   b) Raman spectra are registered and the analysis of the distribution of the intensity of characteristic bands is performed on the UEV,
   c) If it is confirmed that the value of RI for the intensity of the Raman spectrum is lower than the value of RI for the Raman spectrum obtained in an identical way for the sample collected from a healthy individual, the patient is diagnosed with diabetes.

2. The method according to claim 1 wherein the urine sample is subject to centrifugation at 2000×g for about 30 minutes in stage a).

3. The method according to claim 1 wherein, in stage a), the urine sample is concentrated using a dialysis membrane with large-diameter pores permeable for the molecules of the average molecular weight below 1000 kDa (MWCO), which is followed by washing.

4. The method according to claim 1 wherein the washing solution contains silver chloride and sodium dichloroisocyanurate in the amount of 0.1 mg of silver chloride and 4.5 mg of sodium dichloroisocyanurate per litre of the urine sample.

5. The method according to claim 1 wherein the characteristic bands in the Raman spectrum are located in the following ranges: from 980 $cm^{-1}$ to 1020 $cm^{-1}$, from 1110 $cm^{-1}$ to 1140 $cm^{-1}$, from 1420 to 1470 $cm^{-1}$ and from 1565 $cm^{-1}$ to 1710 $cm^{-1}$.

6. The method according to claim 1 wherein, in stage c), in order to determine the change in the intensity of the Raman spectrum, RI is calculated on the basis of the following formula:

$$RI = \frac{I_{AmidI}}{I_{Phenylalanin}} \times a + \frac{I_{Lipids}}{I_{Phenylalanin}}.$$

7. The method according to claim 6 wherein, in stage c), the values of RI for the group of healthy individuals are above 1000, from 1144 to 1164.

8. The method according to claim 6 wherein, in stage c), the values of RI for patients with diabetes are below 600.

9. The method according to claim 6 wherein, in stage c), the values of RI for the group of patients with controlled diabetes are from 550 to 600.

10. The method according to claim 6 wherein, in stage c), the values of RI for the group of patients with uncontrolled diabetes are from 390 to 410.

11. The method according to claim 6 wherein, in stage c), the values of RI for the group of patients with diabetic nephropathy are below 600.

12. The method according to claim 6 wherein, in stage c), the values of RI are below 300 for the group of patients with advanced renal impairment caused by diabetes with the glomerular filtration rate (GFR) below 46 mL/min/1.73 $m^2$.

* * * * *